United States Patent
Zhou et al.

(10) Patent No.: US 11,898,140 B2
(45) Date of Patent: Feb. 13, 2024

(54) HYPERTHERMOPHILIC AEROBIC FERMENTATION INOCULANT PREPARED BY USING MUNICIPAL SEWAGE SLUDGE AND ITS METHOD

(71) Applicant: FUJIAN AGRICULTURE AND FORESTRY UNIVERSITY, Fuzhou (CN)

(72) Inventors: Shungui Zhou, Fuzhou (CN); Zhi Chen, Fuzhou (CN); Hanpeng Liao, Fuzhou (CN)

( * ) Notice: Subject to any disclaimer, the term of this patent is extended or adjusted under 35 U.S.C. 154(b) by 580 days.

(21) Appl. No.: 16/826,261

(22) Filed: Mar. 22, 2020

(65) Prior Publication Data
US 2020/0224153 A1    Jul. 16, 2020

Related U.S. Application Data

(63) Continuation of application No. PCT/CN2018/073426, filed on Jan. 19, 2018.

(51) Int. Cl.
*C12N 1/20* (2006.01)

(52) U.S. Cl.
CPC ............ *C12N 1/20* (2013.01); *C12N 2500/10* (2013.01); *C12N 2500/34* (2013.01)

(58) Field of Classification Search
CPC .. C12N 1/20; C12N 2500/10; C12N 2500/34; C12N 1/205; C12N 1/04; C12R 2001/01; C05F 7/00
See application file for complete search history.

(56) References Cited

U.S. PATENT DOCUMENTS

2005/0032193 A1* 2/2005 Oshima ................... C12N 1/20
                                                                435/252.1
2017/0015577 A1* 1/2017 Nakajima ............. C02F 3/1205

FOREIGN PATENT DOCUMENTS

| CN | 1793330 A | | 6/2006 | |
|---|---|---|---|---|
| CN | 101186889 A | | 5/2008 | |
| CN | 101338295 A | | 7/2009 | |
| CN | 101273757 B | * | 2/2011 | |
| CN | 102660487 A | | 9/2012 | |
| CN | 102703351 A | | 10/2012 | |
| CN | 102851247 A | | 1/2013 | |
| CN | 105060954 A | * | 11/2015 | |
| CN | 107937303 A | | 4/2018 | |
| EP | 2679688 A1 | * | 1/2014 | ............... B09B 3/00 |
| JP | S51115988 A | | 10/1976 | |
| WO | WO-2015145866 A1 | * | 10/2015 | ............. C02F 3/006 |

OTHER PUBLICATIONS

Liao, Hanpeng et al. Development of Hperthermophinic Aerobic Composting and Its Engineering Applications in Organic Solid Wastes. Journal of Fujian Agriculture and Forestry University.

* cited by examiner

*Primary Examiner* — David W Berke-Schlessel
*Assistant Examiner* — Susan E. Fernandez

(57) ABSTRACT

The present disclosure discloses a preparation method for hyperthermophilic aerobic fermentation inoculant prepared by using sewage sludge, the method includes the following steps: carrying out fermentation after the activation of hyperthermophilic aerobic bacteria, removing the supernatant from the fermentation products, and adding the protective agent and stirring until uniform, drying to obtain a product, pulverizing the product by a pulverizer, and sieving the product before sub-packing. The solution of the present disclosure has the following advantages.

8 Claims, 1 Drawing Sheet

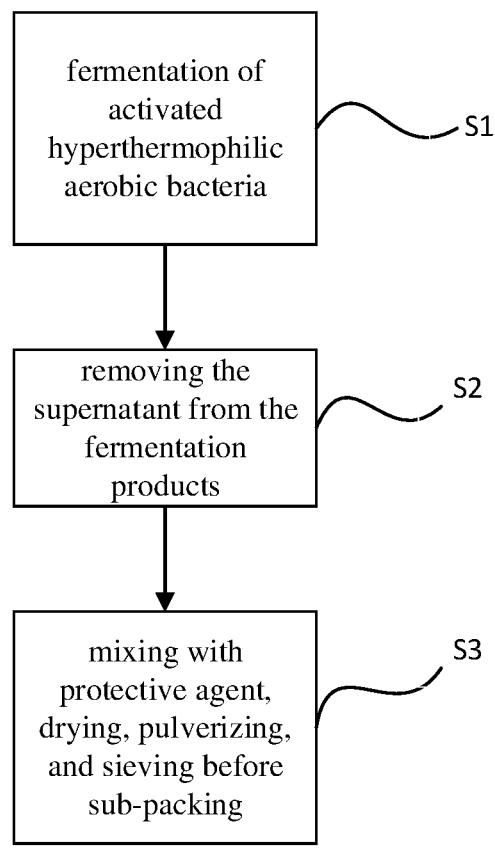

HYPERTHERMOPHILIC AEROBIC FERMENTATION INOCULANT PREPARED BY USING MUNICIPAL SEWAGE SLUDGE AND ITS METHOD

CROSS REFERENCE OF RELATED APPLICATIONS

This application claims all benefits accruing under 35 U.S.C. § 119 from China Patent Application No. 201710906562.6, entitled "HYPERTHERMOPHILIC AEROBIC FERMENTATION INOCULANT PREPARED BY USING MUNICIPAL SEWAGE SLUDGE AND ITS METHOD" filed on Sep. 29, 2017, in the State Intellectual Property Office of China, the content of which is hereby incorporated by reference. This application is a continuation under 35 U.S.C. § 120 of international patent application PCT/CN2018/073426 filed Jan. 19, 2018, the content of which is also hereby incorporated by reference.

TECHNICAL FIELD

The present disclosure relates to the field of microbial culture and application, in particular to a hyperthermophilic aerobic fermentation inoculant prepared by using municipal sewage sludge and its method.

BACKGROUND

Composting is an important technology for the treatment and utilization of organic solid wastes. The essence of composting is the process of decomposition or humification of organic matter driven by microorganisms and release of heat. High temperatures is a double-edged sword for composting. On the one hand, high temperature is benefit for the fast maturity and harmlessness of compost, by promoting the formation of humus and the killing of pathogenic bacteria; on the other hand, the important components of microorganisms such as proteins and nucleic acids are sensitive to temperature, which will suffer irreversible damage and even inactivation as the temperature rises, resulting in inhibition of microbial communities activity. As subsequent, the composting process is hard to run stably. In traditional composting, the best suitable growth temperature for most thermophilic microorganisms is 50 to 60° C., which makes traditional composting have the disadvantages of low compost temperature, slow degradation of organic matter, incomplete killing of pathogenic microorganisms, and long fermentation period.

In 2008, an extreme thermophile bacterium *Calditerricola satsumensis* was used in organic solid waste compost by Y. Oshima from Japan, which effectively increased the temperature of compost and the killing efficiency of pathogens. In 2012, another extreme thermophilic bacterium *Calditerricola yamamurae* was used in sludge compost by Zhou Shungui and co-workers (A extreme thermophilic bacterium UTM801 and its application, patent application number: 201210343222.4, China), and proposed an hyperthermophilic composting technology in China. Compared with traditional composting, hyperthermophilic composting technology can effectively increase the composting temperature, promote the degradation of organic matter, effectively kill pathogenic microorganisms, shorten the fermentation period, leading to reduce the cost of composting. However, the extreme growth conditions of extreme thermophilic bacteria result in a low survival rate in the natural environment, making them easy to be replaced by other local dominant microorganisms or inactivated in practical applications. As subsequent, the treatment effect of hyperthermophilic composting technology was affected. Based on this, it is necessary to regularly add corresponding extreme thermophilic bacteria in practical applications to maintain the communities of extreme thermophilic bacteria in the compost for keeping the technical advantages of hyperthermophilic composting. Thus, production of hyperthermophilic fermentation inoculant through simple fermentation using low-cost organic waste and improving of the activity and storage period of extreme thermophilic bacteria have an important practice meaning for reducing the cost of large-scale industrial application of hyperthermophilic composting technology.

Sewage sludge is the byproduct of wastewater treatment plants. The annual sludge production in China is about 8 million tons in dry weight (about 32 million tons in wet weight), and it is increasing at a rate of 10% to 15% per year. The environmental pollution problem caused by sludge is becoming increasingly prominent, which has caused great safety risks, environmental pressure and economic burden. At the same time, sewage sludge contains nutrients such as carbon, nitrogen, phosphorus, and trace elements that can be used by microorganisms. Preparation of microbial inoculant by sewage sludge fermentation can not only provide a new utilization method of sewage sludge, but also greatly reduce the cost of microbial industrial fermentation. Several patents have reported the use of sludge as the main raw material to produce microbial inoculant in China and other countries. However, extreme thermophilic bacteria with severe growth condition are difficult to preserve, and sewage sludge have limited nutrient contents and unstable ingredients. It will cause slow bacterial growth, low fermentation level and unstable when the sludge is used directly as the sole raw material for fermentation and cultivation. Therefore, no report has been found on the use of sludge for the preparation of hyperthermophilic fermentation inoculant to date.

SUMMARY

The object of the present disclosure is to provide an hyperthermophilic aerobic fermentation inoculant prepared from sewage sludge and its method, so as to improve the fermentation industrial efficiency of extreme thermophilic bacteria and the activity and storage period of the hyperthermophilic fermentation inoculant.

The solution of the present disclosure is provided as below.

A preparation method for hyperthermophilic aerobic fermentation inoculant prepared by using sewage sludge, including the following steps: fermentation was carried out after the activation culture of hyperthermophilic bacteria, followed by removing the supernatant from fermentation, and adding a protective agent and stirring the mixture, drying to obtain the product, pulverizing the product by a pulverizer, and sieving the product and sub-packing.

Preferably, the culture medium used for the fermentation is prepared from sewage sludge.

Preferably, the method for preparing the culture medium used for fermentation is: taking sewage sludge and adding water to regulate the water content of the sludge, and adding antifoaming agents of polyethers, yeast powder, ammonium chloride, sucrose, soluble starch, potassium dihydrogen phosphate, regulating pH, adding composite carrier, mixture well, sterilizing and cooling before use.

Preferably, the protective agent is composed of non-fat milk powder, soluble starch, glycerin, and water.

Preferably, in the protective agent, non-fat milk powder: soluble starch:glycerin:water=(2 to 3):(1 to 2):10:(85 to 87), wherein non-fat milk powder and soluble starch are added by weight, unit is g; glycerin and water are added by volume, unit is mL.

Preferably, the composite carrier is composed of at least one of kaolin, biochar, and wheat bran.

Preferably, the content of the composite carrier is 50-100 g/L.

Preferably, the composite carrier is composed of biochar and wheat bran, and the ratio of the biochar and the wheat bran is 1.5 to 3:1.

Preferably, the solid content of the sludge is 2 to 3%.

Preferably, the hyperthermophilic bacteria is at least one selected from the group consisting of *Thermus thermophilus*, *Calditerricola yamamurae*, *Calditerricola satsumensis*, *Thermaerobacter composti*, *Geobacillus thermocatenulatus* or *Thermaerobacter subterraneus*.

The advantageous effects of the present disclosure are shown as below.

1. Sewage sludge is used as the main raw material for fermentation, which reduces the cost of fermentation, and at the same time provides a way to solve the problem of sludge pollution, which helps to protect and improve the ecological environment;

2. The present disclosure not only reduces the fermentation cost of hyperthermophilic bacteria, but also improves the fermentation efficiency through the adjustment and optimization of sludge culture medium, addressing the problem of hyperthermophilic bacteria inoculant production by fermentation;

3. Compared with the conventional fermentation inoculant, the addition of the composite carrier and the protective agent in the present disclosure can effectively improve the survival rate and storage period of the ultra-high temperature aerobic fermentation inoculant, which is suitable for long-term storage;

4. The production of hyperthermophilic fermentation inoculant through simple fermentation reduces the application cost, which is suitable for large-scale industrial production and application.

BRIEF DESCRIPTION OF THE DRAWING

FIG. 1 is a flow diagram showing a preparation method for a hyperthermophilic aerobic fermentation inoculant prepared by using sewage sludge.

DETAILED DESCRIPTION OF THE EMBODIMENTS

Referring to FIG. 1 which shows a preparation method for a hyperthermophilic aerobic fermentation inoculant prepared by using sewage sludge, comprising the following steps:

S1, fermentation of activated hyperthermophilic aerobic bacteria;

S2, removing the supernatant from the fermentation products, and

S3, mixing with protective agent, drying, pulverizing, and sieving before sub-packing.

In the following detailed embodiments, the present disclosure will be further clarified.

Embodiment 1

Production of *Calditerricola satsumensis* Fermentation Inoculant (1) Sample of Sewage Sludge The concentrated sludge is taken from a sewage treatment plant in Beijing. See Table 1 for the physicochemical properties of the sludge.

TABLE 1

| | Physicochemical properties of the sludge | | | |
|---|---|---|---|---|
| pH | Moisture content (%) | Total carbon content (%) | Total nitrogen content (%) | Total phosphorus content (%) |
| 7.5 | 87.5 | 45.7 | 3.5 | 1.0 |

(2) Preparation of Sludge Medium for Fermentation

Adding water to adjust the solid content of sludge to 2%, adding 0.2% antifoaming agents of polyethers, 1 g/L yeast powder, 0.5 g/L ammonium chloride, 0.3 g/L sucrose, 0.2 g/L soluble starch, 0.3 g/L potassium dihydrogen phosphate, regulating the pH to 7.0, adding composite carrier of 50 g/L biochar/wheat bran (w/w=2/1), mixing evenly, sterilizing at 100° C. for 45 minutes, cooling to 70-80° C. for further use.

(3) *Calditerricola satsumensis* FAFU012 colony was picked from solid medium, and inoculated into 100 mL of CYS liquid medium in 300 mL conical flask, cultured at 80° C., 180 rpm (Revolution(s) Per Minute) for 12 hours. The components of CYS medium are: yeast extract 4.0 g, hydrolyzed casein protein 6.0 g, soluble starch 3.0 g, NaCl 30.0 g, $MgCl_2 \cdot 6H_2O$ 0.27 g, $CaCl_2$ 0.025 g, $FeSO_4 \cdot 7H_2O$ 0.01 g, trace element 100 μL ($Na_2MoO_4 \cdot 2H_2O$ 12.0 g/L, $VOSO_4 \cdot xH_2O$ 1.0 g/L, $MnCl_2$ 5.0 g/L, $ZnSO_4 \cdot 7 H_2O$ 0.6 g/L, $CuSO_4 \cdot 5H_2O$ 0.15 g/L, $CoCl_2 \cdot 6H_2O$ 8.0 g/L, $NiCl_2 \cdot 6H_2O$ 0.2 g/L), and the initial value of pH is 7.5, 0.15 MPa, sterilized at 121° C. for 30 min.

(4) Fermentation of Seed

The above cultures was inoculated into a small fermenter containing a sludge fermentation medium at an inoculation amount of 2%, fermented at 75° C. for 16 hours with ventilation volume of 100 $m^3$/h and stirring speed of 180 rpm.

(5) Large-Scale Fermentation

The seed solution of *Calditerricola satsumensis* FAFU012 was inoculated into the fermentation tank at an inoculation amount of 2%, and fermented at 75° C. for 24 hours with ventilation volume of 100 $m^3$/h and stirring speed of 180 rpm.

(6) Preparation of Fermentation Inoculant

The supernatant of fermentation products was removed by pressure filtration, and a 1% protective agent was added. The protective agent consisted of non-fat milk powder, soluble starch, glycerin, and water. Wherein, non-fat milk powder: soluble starch:glycerin:water=3:2:10:85 (w/w/v/v), the unit of mass is g and the unit of volume is mL. Mixing them at high speed, drying at 90° C., pulverizing by a pulverizer, and sieving through a 80 mesh sieve before sub-packing.

(7) Quality Inspection of the Inoculants

The hyperthermophilic aerobic inoculant produced by fermentation of sludge medium were randomly sampled and tested in accordance with Microbial inoculants in agriculture (GB 20287-2006) of the national standard of the People's Republic of China. After testing, the number of live bacteria was $2.8 \times 10^9$ cfu/g.

Embodiment 2

Production of *Calditerricola yamamurae* Fermentation Inoculant (1) Sample of Sewage Sludge The concentrated sludge is taken from Zhengzhou City, Henan Province. See Table 2 for the physicochemical properties of the sludge.

TABLE 2

Physicochemical properties of the sludge

| pH | Moisture content (%) | Total carbon content (%) | Total nitrogen content (%) | Total phosphorus content (%) |
|---|---|---|---|---|
| 7.6 | 90.2 | 38.9 | 2.7 | 0.8 |

(2) Preparation of Sludge Medium for Fermentation

Adding water to adjust the solid content of sludge to 3%, adding 0.2% antifoaming agents of polyethers, 1.5 g/L yeast powder, 1.0 g/L ammonium chloride, 0.5 g/L sucrose, 0.5 g/L soluble starch, 0.5 g/L potassium dihydrogen phosphate, regulating the pH to 7.0, adding composite carrier of 80 g/L biochar/wheat bran (w/w=1.5/1), mixing evenly, sterilizing at 100° C. for 45 minutes, cooling to 70-80° C. for further use.

(3) *Calditerricola yamamurae* UTM801 colony was picked from solid medium, and inoculated into 100 mL of CYS liquid medium in 300 mL conical flask, cultured at 80° C., 180 rpm (Revolution(s) Per Minute) for 12 hours. The components of CYS medium are: yeast extract 4.0 g, hydrolyzed casein protein 6.0 g, soluble starch 3.0 g, NaCl 30.0 g, $MgCl_2 \cdot 6H_2O$ 0.27 g, $CaCl_2$ 0.025 g, $FeSO_4 \cdot 7H_2O$ 0.01 g, trace element 100 μL ($Na_2MoO_4 \cdot 2H_2O$ 12.0 g/L, $VOSO_4 \cdot xH_2O$ 1.0 g/L, $MnCl_2$ 5.0 g/L, $ZnSO_4 \cdot 7H_2O$ 0.6 g/L, $CuSO_4 \cdot 5H_2O$ 0.15 g/L, $CoCl_2 \cdot 6H_2O$ 8.0 g/L, $NiCl_2 \cdot 6H_2O$ 0.2 g/L), and the initial value of pH is 7.5, 0.15 MPa, sterilized at 121° C. for 30 min.

(4) Fermentation of Seed

The above cultures was inoculated into a small fermenter containing a sludge fermentation medium at an inoculation amount of 2%, fermented at 80° C. for 16 hours with ventilation volume of 100 $m^3/h$ and stirring speed of 180 rpm.

(5) Large-Scale Fermentation

The seed solution of *Calditerricola yamamurae* UTM801 was inoculated into the fermentation tank at an inoculation amount of 2%, and fermented at 80° C. for 24 hours with ventilation volume of 100 $m^3/h$, and stirring speed of 180 rpm.

(6) Preparation of Fermentation Inoculant

The supernatant of fermentation products was removed by pressure filtration, and a 1% protective agent was added. The protective agent consisted of non-fat milk powder, soluble starch, glycerin, and water. Wherein, non-fat milk powder: soluble starch:glycerin:water=3:2:10:85 (w/w/v/v), the unit of mass is g and the unit of volume is mL. Mixing them at high speed, drying at 90° C., pulverizing by a pulverizer, and sieving through a 80 mesh sieve before sub-packing.

(7) Quality Inspection of the Inoculants

The hyperthermophilic aerobic inoculant produced by fermentation of sludge medium were randomly sampled and tested in accordance with Microbial inoculants in agriculture (GB 20287-2006) of the national standard of the People's Republic of China. After testing, the number of live bacteria was $4.5 \times 10^9$ cfu/g.

Embodiment 3

Production of *Thermus thermophilus* Fermentation Inoculant (1) Sample of Sewage Sludge The concentrated sludge is taken from a sewage treatment plant in Fuzhou City, Fujian Province. See Table 3 for the physicochemical properties of the sludge.

TABLE 3

Physicochemical properties of the sludge

| pH | Moisture content (%) | Total carbon content (%) | Total nitrogen content (%) | Total phosphorus content (%) |
|---|---|---|---|---|
| 7.3 | 90.0 | 29.4 | 2.5 | 1.0 |

(2) Preparation of Sludge Medium for Fermentation

Adding water to adjust the solid content of sludge to 3%, adding 0.2% antifoaming agents of polyethers, 1.5 g/L yeast powder, 0.5 g/L ammonium chloride, 0.5 g/L sucrose, 0.5 g/L soluble starch, 1 g/L potassium dihydrogen phosphate, regulating the pH to 7.0, adding composite carrier of 100 g/L biochar/wheat bran (w/w=1.5/1), mixing evenly, sterilizing at 100° C. for 45 minutes, cooling to 70-80° C. for further use.

(3) *Thermus thermophilus* HB8 colony was picked from solid medium, and inoculated into 100 mL of CYS liquid medium in 300 mL conical flask, cultured at 75° C., 180 rpm (Revolution(s) Per Minute) for 12 hours. The components of CYS medium are: yeast extract 4.0 g, hydrolyzed casein protein 6.0 g, soluble starch 3.0 g, NaCl 30.0 g, $MgCl_2 \cdot 6H_2O$ 0.27 g, $CaCl_2$ 0.025 g, $FeSO_4 \cdot 7H_2O$ 0.01 g, trace element 100 μL ($Na_2MoO_4 \cdot 2H_2O$ 12.0 g/L, $VOSO_4 \cdot xH_2O$ 1.0 g/L, $MnCl_2$ 5.0 g/L, $ZnSO_4 \cdot 7H_2O$ 0.6 g/L, $CuSO_4 \cdot 5H_2O$ 0.15 g/L, $CoCl_2 \cdot 6H_2O$ 8.0 g/L, $NiCl_2 \cdot 6H_2O$ 0.2 g/L), and the initial value of pH is 7.5, 0.15 MPa, sterilized at 121° C. for 30 min.

(4) Fermentation of Seed

The above cultures were inoculated into a small fermenter containing a sludge fermentation medium at an inoculation amount of 2%, fermented at 75° C. for 16 hours with ventilation volume of 100 $m^3/h$ and stirring speed of 180 rpm.

(5) Large-Scale Fermentation

The seed solution of *Thermus thermophilus* HB8 was inoculated into the fermentation tank at an inoculation amount of 2%, and fermented at 75° C. for 24 hours with ventilation volume of 100 $m^3/h$, and stirring speed of 180 rpm.

(6) Preparation of Fermentation Inoculant

The supernatant of fermentation products was removed by pressure filtration, and a 1% protective agent was added. The protective agent consisted of non-fat milk powder, soluble starch, glycerin, and water. Wherein, non-fat milk powder: soluble starch:glycerin:water=(2-3):(1-2):10:(85-87) (w/w/v/v), the unit of mass is g and the unit of volume is mL. Mixing them at high speed, drying at 90° C., pulverizing by a pulverizer, and sieving through a 80 mesh sieve before sub-packing.

(7) Quality Inspection of the Inoculants

The hyperthermophilic aerobic inoculant produced by fermentation of sludge medium were randomly sampled and tested in accordance with Microbial inoculants in agriculture (GB 20287-2006) of the national standard of the People's Republic of China. After testing, the number of live bacteria was $2.3 \times 10^9$ cfu/g.

Embodiment 4

Effect of Different Treatments on *Calditerricola* Fermentation and Inoculant Quality (1) Sample of Sewage Sludge The concentrated sludge was taken from a sewage treatment plant in Fuzhou, Fujian Province. The physicochemical properties of the sludge are shown in Table 4.

TABLE 4

Physicochemical properties of the sludge

| pH | Moisture content (%) | Total carbon content (%) | Total nitrogen content (%) | Total phosphorus content (%) |
|---|---|---|---|---|
| 7.5 | 90.3 | 35.4 | 3.1 | 1.0 |

(2) Activation of Fermentation Strains

*Calditerricola satsumensis* FAFU012 colony was picked from solid medium, and inoculated into CYS liquid medium, and cultured at 75° C., 180 rpm (Revolution(s) Per Minute) for 16 hours.

(3) Fermentation and Preparation of the Inoculant

According to different treatments in Table 5, the activated *Calditerricola satsumensis* FAFU012 was subjected to seed fermentation, large-scale fermentation, and microbial inoculant preparation, respectively. Wherein, in seed fermentation, the activated bacterial solution was inoculated into a small fermenter containing a sludge fermentation medium at an inoculation amount of 2%, fermented at 75° C. for 16 hours with ventilation volume of 100 m³/h and stirring speed of 180 rpm; in Large-scale fermentation, the seed solution was inoculated into a fermentation tank at an inoculation amount of 2%, fermented at 75° C. for 24 hours with the pressure of 0.06 Mpa, the ventilation volume of 100 m³/h, and stirring speed of 180 rpm. The supernatant of fermentation products was removed by pressure filtration after fermentation, and the corresponding protective agent was added. Mixing them at high speed evenly, drying at 90° C. to constant weight, pulverizing by a pulverizer, and sieving through a 80 mesh sieve before sub-packing.

TABLE 5

Fermentation and preparation of *Calditerricola satsumensis* FAFU012 inoculant with different schemes

| | Batch | (1) | (2) | (3) | (4) | (5) | (6) | (7) | (8) | (9) | (10) |
|---|---|---|---|---|---|---|---|---|---|---|---|
| Fermentation medium | Solid content of sludge (%) | 4 | 3 | 3 | 3 | 3 | 3 | 3 | 3 | 3 | 3 |
| | pH | 7.0 | 7.0 | 7.0 | 7.0 | 7.0 | 7.0 | 7.0 | 7.0 | 7.0 | 7.0 |
| | Polyether (%) | 0.2 | 0.2 | 0.2 | 0.2 | 0.2 | 0.2 | 0.2 | 0.2 | 0.2 | 0.2 |
| | yeast powder (g/L) | | | | 1.5 | 1.5 | 1.5 | 1.5 | 1.5 | 1.5 | 1.5 |
| | ammonium chloride (g/L) | | 2.0 | 0.5 | 0.5 | 0.5 | 0.5 | 0.5 | 0.5 | 0.5 | 0.5 |
| | Sucrose (g/L) | | | 0.5 | 0.5 | 0.5 | 0.5 | 0.5 | 0.5 | 0.5 | 0.5 |
| | soluble starch (g/L) | | | 1.0 | 0.5 | 0.5 | 0.5 | 0.5 | 0.5 | 0.5 | 0.5 |
| | potassium dihydrogen phosphate (g/L) | | | 1 | 1 | 1 | 1 | 1 | 1 | 1 | 1 |
| Carrier | Kaolin (g/L) | | | | | 50 | | 50 | | | |
| | biochar/wheat bran (1.5/1, g/L) | | | | | | 50 | | | 50 | 50 |
| Protective Agent | Glycerin (%) | 25 | 25 | | | 1 | 1 | | | | |
| | non-fat milk powder: soluble starch: glycerin (3:2:10, %) | | | | | | | 1 | 1 | | 1 |
| | Preservation temperature (° C.) | −20 | normal temperature | normal temperature | normal temperature | normal temperature | normal temperature | normal temperature | normal temperature | normal temperature | normal temperature |

(4) Quality Inspection of Fermentation Products and the Inoculants

TABLE 6

Effect of different schemes on the fermentation and quality of *Calditerricola satsumensis* FAFU012 inoculant

| Batch | Effective live bacteria in fermentation products | Effective live bacteria in the inoculants | |
|---|---|---|---|
| | | 0 day | 15 day |
| (1) | $2.3 \times 10^5$ cfu/mL | $1.0 \times 10^5$ cfu/mL | 0 |
| (2) | $2.3 \times 10^5$ cfu/mL | $1.0 \times 10^5$ cfu/mL | $3.1 \times 10^2$ cfu/mL |
| (3) | $3.6 \times 10^6$ cfu/mL | $3.6 \times 10^6$ cfu/mL | $2.6 \times 10^2$ cfu/mL |
| (4) | $2.4 \times 10^9$ cfu/mL | $2.4 \times 10^9$ cfu/mL | $3.6 \times 10^3$ cfu/mL |
| (5) | $3.6 \times 10^9$ cfu/mL | $2.6 \times 10^8$/g | $1.6 \times 10^6$/g |
| (6) | $1.2 \times 10^9$ cfu/mL | $2.1 \times 10^9$/g | $3.6 \times 10^6$/g |
| (7) | $3.4 \times 10^9$ cfu/mL | $1.2 \times 10^8$/g | $2.6 \times 10^8$/g |
| (8) | $3.8 \times 10^9$ cfu/mL | $2.3 \times 10^8$/g | $3.3 \times 10^5$ cfu/mL |
| (9) | $3.4 \times 10^9$ cfu/mL | $2.8 \times 10^9$/g | $2.6 \times 10^7$/g |
| (10) | $2.8 \times 10^9$ cfu/mL | $3.1 \times 10^9$/g | $2.7 \times 10^9$/g |

The above results show that compared with other schemes, the *Calditerricola* inoculant prepared in the present disclosure has high effective live bacteria and good preservation effect.

What is claimed is:

1. A preparation method for a hyperthermophilic aerobic fermentation inoculant prepared by using sewage sludge, comprising:

fermenting hyperthermophilic aerobic bacteria to obtain a fermentation broth,
removing supernatant from the fermentation broth,
mixing the fermentation broth with protective agent to obtain a mixture,
drying the mixture,
pulverizing the dried mixture, and
sieving the pulverized mixture for packing;
wherein a culture medium for the fermentation is prepared by:
  taking sewage sludge and adding water to the sewage sludge to regulate a solid content of the sewage sludge;
  adding antifoaming agents of polyethers, yeast powder, ammonium chloride, sucrose, soluble starch, and potassium dihydrogen phosphate to the sewage sludge;
  regulating pH of the sewage sludge;
  adding composite carrier into the sewage sludge, and stirring the sewage sludge for uniformly mixing the composite carrier and the sewage sludge;
  sterilizing the mixture of the composite carrier and the sewage sludge; and
  cooling the sewage sludge to obtain the culture medium for the fermentation.

2. The preparation method according to claim 1, wherein the protective agent is composed of non-fat milk powder, soluble starch, glycerin, and water.

3. The preparation method according to claim 1, wherein the protective agent comprises 2 to 3 g non-fat milk powder, 1 to 2 g soluble starch, 10 mL glycerin, and 85 to 87 mL water.

4. The preparation method according to claim 1, wherein the composite carrier is composed of at least one selected from the group consisting of kaolin, biochar, and wheat bran.

5. The preparation method according to claim 1, wherein the content of the composite carrier is 50 to 100 g/L.

6. The preparation method according to claim 1, wherein the solid content of the sludge is regulated to 2 to 3% by the addition of the water.

7. The preparation method according to claim 1, wherein the composite carrier is composed of biochar and wheat bran, and a mass ratio of the biochar to the wheat bran is 1.5:1 to 3:1.

8. The preparation method according to claim 1, wherein the hyperthermophilic aerobic bacteria is at least one selected from the group consisting of *Thermus thermophilus, Calditerricola yamamurae, Calditerricola satsumensis, Thermaerobacter composti, Geobacillus thermocatenulatus* or *Thermaerobacter subterraneus*.

* * * * *